(12) United States Patent
Mochly-Rosen

(10) Patent No.: US 7,081,444 B2
(45) Date of Patent: Jul. 25, 2006

(54) ΨεRACK PEPTIDE COMPOSITION AND METHOD FOR PROTECTION AGAINST TISSUE DAMAGE DUE TO ISCHEMIA

(75) Inventor: Daria Mochly-Rosen, Menlo Park, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 151 days.

(21) Appl. No.: 10/807,553

(22) Filed: Mar. 22, 2004

(65) Prior Publication Data

US 2004/0186055 A1 Sep. 23, 2004

Related U.S. Application Data

(63) Continuation of application No. 10/007,363, filed on Nov. 9, 2001, now abandoned.

(60) Provisional application No. 60/247,830, filed on Nov. 10, 2000.

(51) Int. Cl.
*C07K 14/00* (2006.01)
(52) U.S. Cl. .......................... 514/2; 530/350
(58) Field of Classification Search ............. 514/2; 530/350
See application file for complete search history.

(56) References Cited

U.S. PATENT DOCUMENTS

| 6,165,977 | A | 12/2000 | Mochly-Rosen |
| 6,329,349 | B1 | 12/2001 | Liang et al. |
| 6,855,693 | B1 * | 2/2005 | Mochly-Rosen et al. ..... 514/12 |

OTHER PUBLICATIONS

Chen et al. Oct. 1, 2001; Chemistry & Biology 8:1123-1129.*
Dorn, G.W., et al., *PNAS* 96(22):12798-12803, (1999).
Hahn, H.S., et al., *Circulation* 102(18): Abstract No. 770, (2000).
Ron and Mochly-Rosen, *Proc. Natl. Acad. Sci USA* 92:492-496, (1995).

* cited by examiner

*Primary Examiner*—Karen Cochrane Carlson
(74) *Attorney, Agent, or Firm*—Judy M. Mohr; Perkins Coie LLP

(57) ABSTRACT

A method of reducing damage to cells and tissue caused by an ischemic or hypoxic event is disclosed. The method includes administering to the cell or tissue, either in vivo or ex vivo, ψεRACK peptide. The peptide can be administered before, during or after the ischemic or hypoxic event.

35 Claims, 4 Drawing Sheets

* P<0.05

ΨεRACK PEPTIDE COMPOSITION AND METHOD FOR PROTECTION AGAINST TISSUE DAMAGE DUE TO ISCHEMIA

This application is a continuation of U.S. application Ser. No. 10/007,363 filed Nov. 9, 2001, now abandoned; which claims the benefit of U.S. Provisional Application No. 60/247,830 filed Nov. 10, 2000, both of which are incorporated herein by reference in their entirety.

This work was supported in part by The National Institutes of Health Grant HL52141. Accordingly, the United States Government has certain rights in this invention.

FIELD OF THE INVENTION

The present invention relates to a method of protecting cells and tissues from damage due to an ischemic event. The method involves administering a peptide agonist of protein kinase C, and more specifically, administering a pseudo-epsilon RACK (ψεRACK) peptide.

REFERENCES

Brew, E. C., et al., *Am. J. Physiol* 269(Heart Circ. Physiol. 38):H1370–H1378 (1995).
Colbert, M. C. et al., *J. Clin. Invest.* 100:1958 (1997).
Csukai, M., et al., 9$^{TH}$ INTERNATIONAL CONFERENCE ON SECOND MESSENGERS AND PHOSPHOPROTEINS 112 (1995).
Csukai, M., et al, *J. Biol. Chem.*, 272:29200–29206 (1997).
Disatnik, M. H., et al., *Exp. Cell Res.* 210:287–297 (1994).
Dorn, G., *Proc. Natl. Acad. Sci. USA* 96(22): 12798 (1999).
Fawell et al., *Proc. Natl. Acad. Sci. USA* 91:664–68 (1994).
Gray, M. O. et al., *J. Biol. Chem.,* 272:30945–3095 (1997).
Hu, K. and Nattel, S., *Circulation* 92:2259–2265 (1995).
Johnson, J. A., et al., *J. Biol. Chem.* 271:24962–24966 (1996).
Johnson, J. A. et al., *Circ. Res.*, 79:1086 (1996a).
Lindgren et al., *Trends. Pharmacol. Sci.,* 21:99–103 (2000).
Liu, Y., et al., *J. Mol. Cell. Cardiol.* 27:883–892 (1995).
Mitchell, M. B., et al., *Circulation* 88:1633 (1993).
Mitchell, M. B., et al., *Circ. Res.* 76:73–81 (1995).
Mitchell et al., *J. Peptide Res.,* 56:318–325 (2000).
Mochly-Rosen, D., et al., *Molec. Biol. Cell* (formerly *Cell Reg.*) 1:693–706 (1990).
Mochly-Rosen, D., et al., *Proc. Natl. Acad. Sci. USA* 88:3997–4000 (1991).
Mochly-Rosen, D., et al., *J. Biol. Chem.,* 226:1466–1468 (1991a).
Mochly-Rosen, D., et al., *Science* 268:247–251 (1995).
Murry, C. E., et al., *Circulation* 74:1123–1136 (1986).
Papadopoulos, V. and Hall, P. F. *J. Cell Biol.* 108:553–567 (1989).
Pitcher, J., et al., *Science* 257:1264–1267 (1992).
Rolhbard et al., *Nature Med.,* 6:1253–1257 (2000).
Ron, D., et al., *Proc. Natl. Acad. Sci. USA* 91:839–843 (1994).
Ron, D., et al., *Biol. Chem.* 279:24180–24187 (1995).
Saito, N. et al., *Proc. Natl. Acad. Sci. USA* 86:3409–3413 (1989).
Schultz, J. E. J., et al., *Circ. Res.* 78:1100–1104 (1996).
Schwarlze et al., *Trends. Pharmacol. Sci.,* 21:45–48 (2000).
Smith, B. L. and Mochly-Rosen, D., *Biochem. Biophys. Res. Commun.* 188:1235–1240 (1992).
Speechly-Dick, M. E., et al., *Circ. Res.* 75:586–590 (1993).
Stebbins, E. G., et al., *J. Biol. Chem.,* 276:29644–29650 (2001).
Théodore L., et al., *J. Neurosci.* 15:7158 (1995).
Vives et al. *J. Biol. Chem.,* 272:16010–16017 (1997).

BACKGROUND OF THE INVENTION

Protein kinase C (PKC) is a key enzyme in signal transduction involved in a variety of cellular functions, including cell growth, regulation of gene expression and ion channel activity. The PKC family of isozymes includes at least 11 different protein kinases which can be divided into at least three subfamilies based on their homology and sensitivity to activators. Members of the classical or cPKC subfamily, α, $β_I$, $β_{II}$ and γPKC, contain four homologous domains (C1, C2, C3 and C4) inter-spaced with isozyme-unique (variable or V) regions, and require calcium, phosphatidylserine (PS), and diacylglycerol (DG) or phorbol esters for activation. Members of the novel or nPKC subfamily, δ, ε, η, and θPKC, lack the C2 homologous domain and do not require calcium for activation. Finally, members of the atypical or aPKC subfamily, ζ and λ/ιPKC, lack both the C2 and one half of the C1 homologous domains and are insensitive to DG, phorbol esters and calcium.

Studies on the subcellular distribution of PKC isozymes demonstrate that activation of PKC results in its redistribution in the cells (also termed translocation), such that activated PKC isozymes associate with the plasma membrane, cytoskeletal elements, nuclei, and other subcellular compartments (Saito, et al., 1989; Papadopoulos and Hall, 1989; Mochly-Rosen, et al., 1990).

It appears that the unique cellular functions of different PKC isozymes are determined by their subcellular location. For example, activated $β_I$PKC is found inside the nucleus, whereas activated $β_{II}$PKC is found at the perinucleus and cell periphery of cardiac myocytes (Disatnik, et al., 1994). Further, in the same cells, εPKC binds to cross-striated structures (possibly the contractile elements) and cell-cell contacts following activation or after addition of exogenous activated εPKC to fixed cells (Mochly-Rosen, et al., 1990; Disatnik, et al., 1994). The localization of different PKC isozymes to different areas of the cell in turn appears due to binding of the activated isozymes to specific anchoring molecules termed Receptors for Activated C-Kinase (RACKs).

RACKs are thought to function by selectively anchoring activated PKC isozymes to their respective subcellular sites. RACKs bind only fully activated PKC, but RACKs are not necessarily substrates of the enzyme nor is the binding to RACKs mediated via the catalytic domain of the kinase (Mochly-Rosen, et al., 1991). Translocation of PKC reflects binding of the activated enzyme to RACKs anchored to the cell particulate fraction and the binding to RACKs is required for PKC to produce its cellular responses (Mochly-Rosen, 1995). Inhibition of PKC binding to RACKs in vivo inhibits PKC translocation and PKC-mediated function (Johnson, et al., 1996; Ron, et al., 1995; Smith and Mochly-Rosen, 1992).

cDNA clones encoding RACK1 and RACK2 have been identified (U.S. Pat. No. 5,519,003; Ron, et al., 1994; Csukai, et al., 1995). Both are homologs of the β subunit of G proteins, a receptor for another translocating protein kinase, the β-adrenergic receptor kinase, βARK (Pitcher, et al., 1992). Similar to Gβ, RACK1, and RACK2 have seven WD40 repeats (Ron, et al., 1994; Csukai, et al., 1995).

Recent data suggest that RACK1 is a $\beta_{II}$PKC-specific RACK (Stebbins et al., 2001) whereas RACK2 is specific for activated $\epsilon$PKC (Csukai et al., 1997).

Translocation of PKC is required for proper function of PKC isozymes. Peptides that mimic either the PKC-binding site on RACKs (Mochly-Rosen, 1991a; Mochly-Rosen, 1995) or the RACK-binding site on PKC (Ron, et al., 1995; Johnson, et al., 1996) are isozyme-specific translocation inhibitors of PKC that selectively inhibit the function of the enzyme in vivo. For example, an eight amino acid peptide derived from $\epsilon$PKC (peptide $\epsilon$V1-2; SEQ ID NO:1, Glu Ala Val Ser Leu Lys Pro Thr) is described in U.S. Pat. No. 6,165,977. The peptide contains a part of the RACK-binding site on $\epsilon$PKC and selectively inhibits specific $\epsilon$PKC-mediated functions in cardiac myocytes.

Recently, PKC and more specifically $\epsilon$PCK have been shown to be involved in cardiac preconditioning to provide protection from ischemic injury. Prolonged ischemia causes irreversible myocardium damage primarily due to death of cells at the infarct site. Studies in animal models, isolated heart preparations and isolated cardiac myocytes in culture have demonstrated that short bouts of ischemia of cardiac muscle reduce such tissue damage in subsequent prolonged ischemia (Liu, Y., et al., 1995, 1996; Hu, et al., 1995; Brew, et al., 1995; Schultz, et al., 1996). This protection, which occurs naturally following angina and has been termed preconditioning, can be mimicked by a variety of non-specific PKC agonists (Mitchell et al., 1993; Mitchell et al., 1995; Murry et al., 1986; Speechly-Dick et al., 1994). Both $\delta$PKC and $\epsilon$PKC activation occurs following preconditioning (Gray et al., 1997), however, $\epsilon$PKC activation is required for protection of cardiac myocytes from ischemia-induced cell death (U.S. Pat. No. 6,165,977).

In a recent study, an $\epsilon$PKC-selective peptide agonist was shown to provide cardio-protection from ischemia when administered intracellulary to isolated neonatal and adult cardiomyocytes and when produced intracellulary in vivo in transgenic mice (Dorn G. et al., 1999). In this work, a $\epsilon$PKC peptide agonist was administered intracellulary to isolated cells in vitro by laboratory techniques suitable at the cellular level or by genetic transfection. Unfortunately, neither of these techniques are suitable or likely to be successful for human therapy. Moreover, it is unknown from this work whether or not the $\epsilon$PKC peptide could be delivered extracellulary to whole tissue or intact organs in vivo to achieve a therapeutic effect.

SUMMARY OF THE INVENTION

Accordingly, it is an object of the invention to provide a method of protecting tissue from damage due to an ischemic event.

It is a further object of the invention to provide a method of administering an $\epsilon$PKC peptide agonist for induction of ischemic preconditioning.

It is yet another object of the invention to provide a method of ameliorating damage to tissue caused by an ischemic event.

Accordingly, in one aspect, the invention includes a method of reducing injury to a cell exposed to an ischemic or an hypoxic condition by administering to the cell a $\psi$$\epsilon$RACK peptide. In one embodiment, the peptide is administered prior to exposing the cell to the ischemic or hypoxic condition. For example, the peptide administered for a period of time of between about 1–180 minutes prior to exposing the cell to ischemia or hypoxia. In another embodiment, the peptide is administered after the cell is exposed to an ischemic or hypoxic condition. For example, the peptide is administered for between about 1–180 minutes after the cell is exposed to an ischemic or hypoxic condition. In another embodiment, the peptide is administered during to the cell during the period of ischemia or hypoxia.

In one embodiment, the $\psi$$\epsilon$RACK peptide has a sequence identified as SEQ ID NO:2. In other embodiments, the peptide has a sequence selected from the group consisting of SEQ ID NOS:6–18.

In yet another embodiment, the $\psi$$\epsilon$RACK peptide is linked to a moiety effective to facilitate transport across a cell membrane, such as a Tat-derived peptide (SEQ ID NO:5), an Antennapedia carrier peptide (SEQ ID NO:3), or a polyarginine peptide.

The peptide can be administered by a route selected from the group consisting or intraveneous, parenteral, subcutaneous, inhalation, intranasal, sublingual, mucosal, and transdermal.

In another aspect, the invention includes a method of reducing injury to tissue exposed to an ischemic or an hypoxic condition by administering to the tissue a $\psi$$\epsilon$RACK peptide, as described above.

These and other objects and features of the invention will be more fully appreciated when the following detailed description of the invention is read in conjunction with the accompanying drawings.

BRIEF DESCRIPTION OF THE SEQUENCES

Figure 1A:
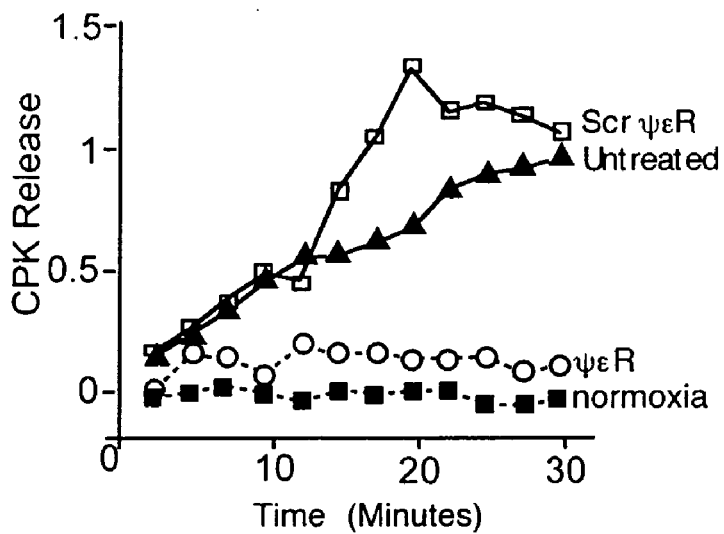
FIG. 1A shows creatine phosphokinase (CPK) release as a function of time during reverse perfusion in ex vivo rat hearts treated with $\psi$$\epsilon$RACK (open circles) or with scrambled $\psi$$\epsilon$RACK (control, open squares) prior to an ischemic event. The treated hearts were compared to hearts subjected to the ischemic period but left untreated (closed triangles) and to hearts maintained under normoxia conditions (no ischemia, no peptide treatment; closed squares) as controls.

SEQ ID NO:1 is a prior art (U.S. Pat. No. 6,165,977) εPKC octapeptide.

SEQ ID NO:2 is a ψεRACK octapeptide

SEQ ID NO:3 is the Drosophila Antennapedia homeodomain-derived carrier peptide.

SEQ ID NO:4 is a scrambled ψεRACK octapeptide.

SEQ ID NO:5 is a Tat-derived carrier peptide.

SEQ ID NO:6 is a modification of SEQ ID NO:2.

SEQ ID NO:7 is a modification of SEQ ID NO:2.

SEQ ID NO:8 is a modification of SEQ ID NO:2.

SEQ ID NO:9 is a modification of SEQ ID NO:2.

SEQ ID NO:10 is a modification of SEQ ID NO:2.

SEQ ID NO:11 is a modification of SEQ ID NO:2.

SEQ ID NO:12 is a modification of SEQ ID NO:2.

SEQ ID NO:13 is a modification of SEQ ID NO:2.

SEQ ID NO:14 is a modification of SEQ ID NO:2.

SEQ ID NO:15 is a modification of SEQ ID NO:2.

SEQ ID NO:16 is a modification of SEQ ID NO:2.

SEQ ID NO:17 is a modification of SEQ ID NO:2.

SEQ ID NO:18 is a fragment of SEQ ID NO:2.

DETAILED DESCRIPTION OF THE INVENTION

I. Definitions

"Tissue" as used herein refers to a group of similarly specialized cells that perform a common function. Tissues compose the organs and structural components of living organisms. As used herein, tissue is intended to include an organ composed of a given tissue and to the cells, individually or collectively, that compose the tissue.

"Ischemia" or an "ischemic event" refers to an insufficient supply of blood to a specific cell, tissue or organ. A consequence of decreased blood supply is an inadequate supply of oxygen to the organ or tissue (hypoxia). Prolonged hypoxia may result in injury to the affected organ or tissue.

"Anoxia" refers to a virtually complete absence of oxygen in the organ or tissue, which, if prolonged, may result in death of the cell, organ or tissue.

"Hypoxia" or a "hypoxic condition" intends a condition under which a cell, organ or tissue receives an inadequate supply of oxygen.

"Ischemic injury" refers to cellular and/or molecular damage to an organ or tissue or cell as a result of a period of ischemia.

"Hypoxic injury" refers to damage to a cell, organ, or tissue due to a period of inadequate oxygen supply.

"Reperfusion" refers to return of fluid flow into a tissue after a period of no-flow or reduced flow. For example, in reperfusion of the heart, fluid or blood returns to the heart through a supply line, such as the coronary arteries in vivo, after removal of an occlusion to the fluid or blood supply.

"Treating a disease" refers to administering a therapeutic substance effective to reduce the symptoms of the disease and/or lessen the severity of the disease.

"Conservative amino acid substitutions" are substitutions which do not result in a significant change in the activity (e.g., εPKC-agonist activity or ψεRACK-agonist activity) or tertiary structure of a selected polypeptide. Such substitutions typically involve replacing a selected amino acid residue with a different residue having similar physicochemical properties. For example, substitution of Glu for Asp is considered a conservative substitution since both are similarly-sized negatively-charged amino acids. Groupings of amino acids by physico-chemical properties are known to those of skill in the art.

With respect to a specific sequence, "conservative substitutions thereof" refers to sequences that differ from the specific sequence by having conservative amino acid substitutions at one or more positions.

"Peptide" and "polypeptide" are used interchangeably herein and refer to a compound made up of a chain of amino acid residues linked by peptide bonds. Unless otherwise indicated, the sequence for peptides is given in the order from the amino termiums to the carboxyl terminus.

When a first peptide or polypeptide is said to "correspond" or to be "homologous" to a second peptide or polypeptide fragment, it means that the peptide or fragments have a similarity in amino acid residues if they have an alignment score of >5 (in standard deviation units) using the program ALIGN with the mutation gap matrix and a gap penalty of 6 or greater (Dayhoff, M. O., in ATLAS OF PROTEIN SEQUENCE AND STRUCTURE (1972) Vol. 5, National Biomedical Research Foundation, pp. 101–110, and Supplement 2 to this volume, pp. 1–10.) The two sequences (or parts thereof) are more preferably homologous if their amino acids are greater than or equal to 50%, more preferably 70%, still more preferably 80%, identical when optimally aligned using the ALIGN program mentioned above.

A polypeptide sequence or fragment is "derived" from another polypeptide sequence or fragment when it has an identical sequence of amino acid residues as a region of the another sequence or fragment.

An "εPKC agonist peptide" or "εPKC specific agonist peptide" is understood to mean a peptide between about 4 and about 30, preferably between about 5 and about 15, amino acids in length that is derived from εPKC. In one embodiment, the εPKC agonist peptide is derived from the region of εPKC between about amino acids 70 and 120, preferably between about amino acids 80 and 100, more preferably between about amino acids 85 and 92.

Abbreviations: "PKC", protein kinase C; "RACK", receptor for activated C-kinase.

Abbreviations for amino acid residues are the standard 3-letter and/or 1-letter codes used in the art to refer to one of the 20 common L-amino acids.

II. Administration of ψεRACK Peptide Agonist

In one aspect, the invention provides a method of protecting a cell, a tissue, or an organ from damage due to an ischemic event or a hypoxic condition by administering a peptide capable of activating signaling proteins, such as PKC, that are activated in vivo by binding to a cognate polypeptide such as a receptor protein (RACK). Regions of homology between the PKC signaling peptide and its RACK are termed "pseudo-RACK" sequences (ψ-RACK; Ron et al, 1994, 1995) and typically have a sequence similar to the PKC-binding region of the corresponding RACK. A ψ-RACK sequence that acts as an εPKC specific agonist peptide is identified herein as SEQ ID NO:2. This peptide, referred to herein as ψεRACK, is an εPCK specific agonist peptide and induces translocation of εPKC. Heretofore, studies have focussed on identifying drugs and peptidomimetics that mimic the action of ψεRACK, as it was unknown if the peptide itself could be administered in vivo or ex vivo to a whole organ to induce translocation of εPCK to confer protection from ischemia. In studies performed in support of the invention, ψεRACK was administered ex vivo and in vivo to whole hearts prior to and after exposure to an ischemic condition. The peptide reduced the extent of ischemic injury, as will now be described.

A. Administration of ψεRACK Peptide Agonist Prior to Ischemia

A peptide having the sequence identified herein as SEQ ID NO:2 was synthesized and purified as described in the Methods section. A scrambled ψεRACK peptide (SEQ ID NO:4) was also prepared to serve as a comparison or a negative control to the ψεRACK peptide. In some studies, the peptides were conjugated to a carrier peptide, such as Drosophila Antennapedia homeodomain (SEQ ID NO:3). It will be appreciated that administration of the native peptide, that is the peptide unmodified by attachment to a carrier, is also contemplated. Carrier peptides other than Drosophila Antennapedia are also contemplated, and other exemplary carrier peptides include Tat-derived peptide (SEQ ID NO:5, Fawell et al., 1994, Vives et al., 1997) or a polyarginine peptide (Mitchell et al., 2000; Rolhbard et al., 2000), or other like carries described in the art (Lindgren et al., 2000; Schwarlze et al., 2000).

Animals were anesthetized as described in Example 1 and their hearts were rapidly removed and cannulated for perfusion on a Langendorff apparatus. Hemodynamic parameters were monitored until stabilized, typically for 10–20 minutes. After equilibration, ψεRACK peptide (SEQ ID NO:2) or a scrambled ψεRACK peptide (SEQ ID NO:4) were delivered to the hearts via the coronary arteries using 0.5 μM of peptide for 20 minutes.

To induce global ischemia, flow to the hearts was interrupted for 45 minutes. The hearts were then reperfused for 30 minutes. During reperfusion, ischemia-induced cell damage was determined by measuring the activity of creatine phosphokinase (absorbance at 520 nm) in the perfusate. Creatine phosphokinase is a cytosolic enzyme in cardiac myocytes and its presence in the perfusate is proportional to the number of cardiomyocytes damaged by the ischemia. The results are shown in FIGS. 1A–1B.

FIG. 1A shows the creatine phosphokinase (CPK) release as a function of time during the 30 minute reperfusion of ex vivo hearts treated with 500 nM (0.5 μM) ψεRACK (open circles) or with 0.5 μM scrambled ψεRACK (open squares) prior to the ischemic event. Also shown is the CPK release for hearts subjected to the ischemic period but untreated with a peptide (closed triangles) and to hearts maintained under normoxia conditions (no ischemia, no peptide treatment; closed squares), as controls. The hearts treated with ψεRACK prior to ischemia have a release of CPK close to the control hearts maintained under normoxia conditions. In contrast, hearts treated with scrambled ψεRACK have significant release of CPK, indicating significant cell damage.

Figure 1B:
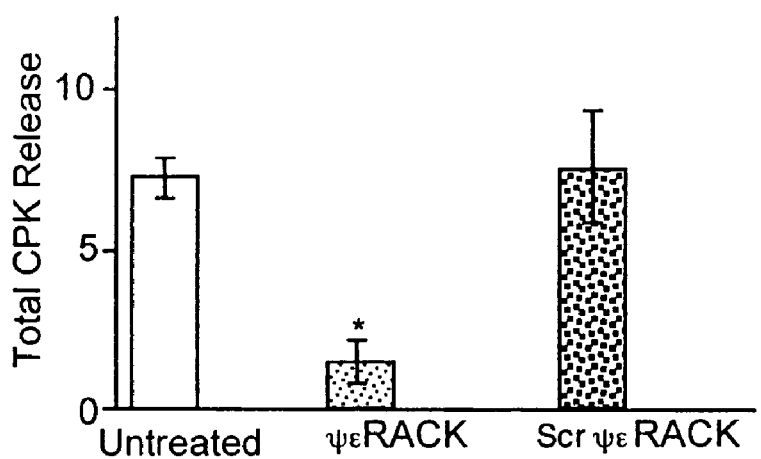
FIG. 1B shows the total amount of CPK released in the study described in FIG. 1A during 30 minutes of reperfusion.

FIG. 1B is a bar graph showing the total CPK release during the reperfusion period for the hearts treated with ψεRACK and with scrambled ψεRACK. The total CPK release from hearts exposed to the ischemic event but left untreated are also shown.

FIGS. 1A–1B show that hearts treated with ψεRACK prior to an ischemic event provides protection from damage resulting from a subsequent ischemic event. Accordingly, in one embodiment the invention contemplates a method of reducing or preventing injury to a tissue exposed to an ischemic or hypoxic event by administering to the tissue an amount of ψεRACK agonist peptide. The peptide can be administered from between 1–180 minutes prior to the ischemic event, more preferably from about 1–120 minutes prior to the ischemic event, more preferably from about 1–60 minutes prior to the ischemic event. In another embodiment, a time period of no more than about 180 minutes, more preferably no more than 120 minutes, still more preferably no more than about 60 minutes, lapses between cessation of peptide delivery and the ischemic event.

In another study in support of the invention, the functional recovery of ex vivo hearts after an ischemic event was evaluated by monitoring the isovolumic left ventricle pressure (LVP) at a constant pacing (3.3 Hz) and at a constant coronary flow (10 mL/min), as described in Example 1. Prior to the ischemic event, the hearts were treated with 500 nM ψεRACK (SEQ ID NO:2) or with scrambled ψεRACK peptide (SEQ ID NO:4). After the 30 minute global ischemia, the hearts were monitored during a 30 minute reperfusion period. The results are shown in FIGS. 2A–2B.

Figure 2A:
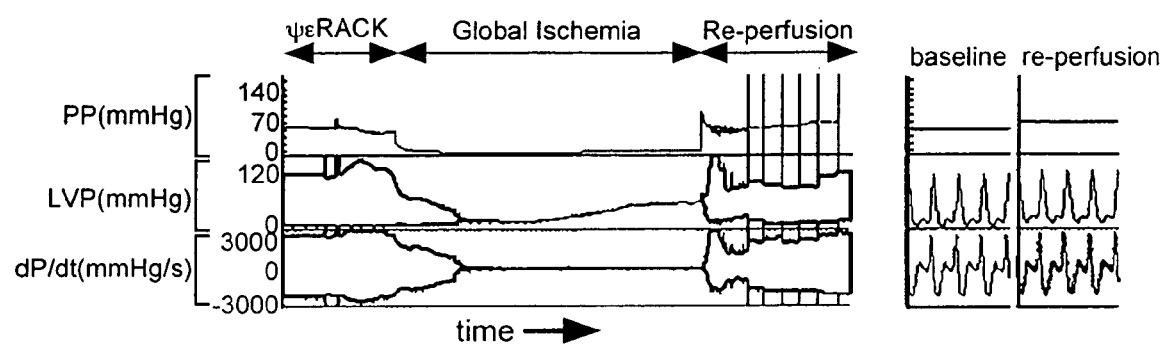
FIG. 2A shows the functional recovery of a working heart perfused with $\psi$$\epsilon$RACK prior to global ischemia, where the left ventricle developed pressure (LVP, in mmHg), its first derivative (dP/dt, in mmHg/sec), and the coronary perfusion pressure (PP, in mmHg) are shown. The right panel shows an expansion of the same trace before (baseline) and after reperfusion.
Figure 2B:
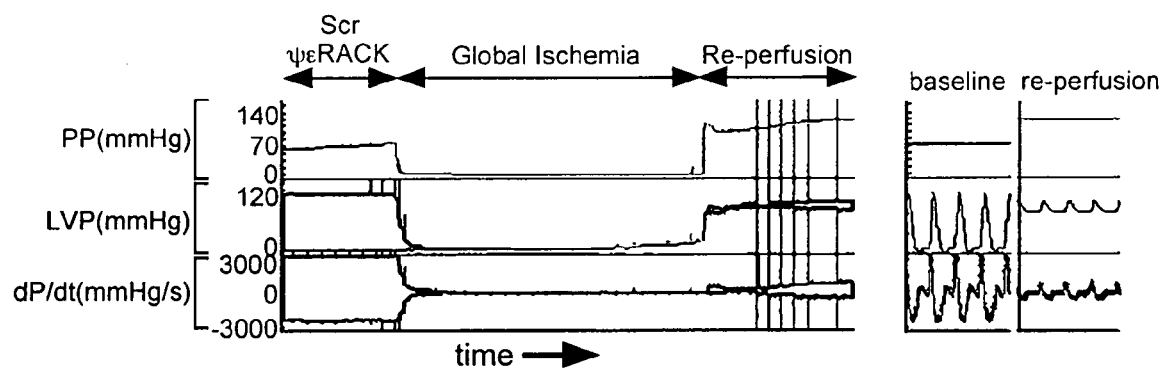
FIG. 2B is a scan similar to FIG. 2A for a working heart perfused with scrambled $\psi$$\epsilon$RACK prior to ischemia.

FIG. 2A shows the results for the hearts treated with ψεRACK peptide prior to global ischemia, and FIG. 2B shows the results for hearts treated with scrambled ψεRACK prior to ischemia. In comparing the baseline levels and reperfusion levels of the treated and untreated hearts, it is seen that administration of ψεRACK peptide before ischemia significantly reduced the ischemic injury. This is particularly evidenced by comparing the recovery of left ventricle developed pressure (LVP) in the hearts pre-treated with ψεRACK to those pre-treated with the scrambled peptide. A four-fold improvement in both the LVP recovery and its first derivative (dP/dt) were achieved by pre-treating with ψεRACK. Furthermore, ψεRACK reduced the elevated LVP end diastolic pressure and the coronary perfusion pressure (PP).

Accordingly, these studies (FIGS. 1 and 2) show that cellular damage to a tissue due to ischemic or hypoxia is reduced by administering ψεRACK prior to the ischemic event or the hypoxic event. In this study, the ψεRACK was administered through the coronary arteries to the organ and for a period prior to exposure to the ischemic and/or hypoxic condition. The time period, as well as the dose of peptide administered, can vary considerably, as will be discussed in more detail below.

B. Administration of ψεRACK Peptide Agonist Subsequent to Ischemia

In another study performed in support of the invention, ψεRACK was administered to hearts ex vivo after a prolonged ischemic period and was effective to provide protection from ischemic injury. As described in Example 2, whole rat hearts were perfused on a Langendorff apparatus. After a 30 minute equilibration period, global ischemia was induced by stopping fluid flow for 45 minutes. The hearts were then reperfused with or without ψεRACK peptide for 20 minutes, followed by 40 minutes perfusion without peptide. During the 60 minutes following ischemia (20 minutes of peptide reperfusion plus 40 minutes perfusion), the CPK activity in the perfusate was analyzed. The results are shown in FIGS. 3A–3B.

Figure 3A:
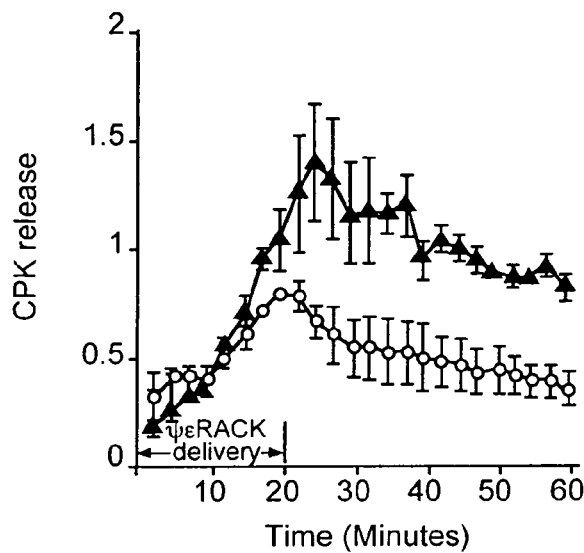
FIG. 3A shows CPK release as a function of time following ischemic insult in ex vivo rat hearts treated for the first 20 minutes of reperfusion with $\psi$$\epsilon$RACK (open circles) and in hearts left untreated after ischemia (solid triangles).
Figure 3B:
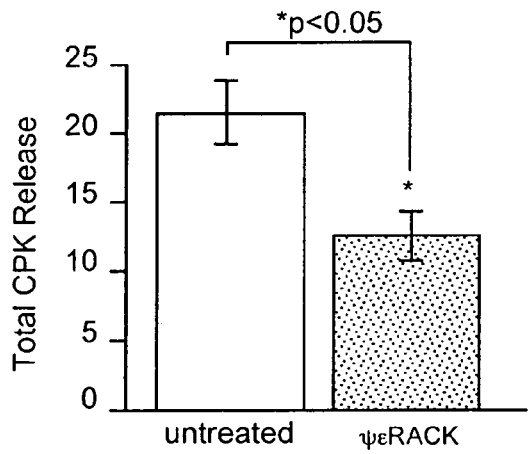
FIG. 3B is a bar graph showing the total CPK release during a 60 minute reperfusion period following an ischemic insult to whole rat hearts (i) treated ex vivo with $\psi$$\epsilon$RACK for 20 minutes after the ischemic insult, or (ii) left untreated.

FIG. 3A shows the CPK release as a function of time following ischemia for hearts treated with ψεRACK (open circles) and for hearts left untreated after ischemia (solid triangles). FIG. 3B is a bar graph showing the total CPK release during the 60 minute perfusion period for the peptide treated and untreated ex vivo hearts. The data shows that subsequent administration of ψεRACK peptide to tissue previously exposed to an ischemic or hypoxic condition is effective to reduce the cellular damage. FIG. 3B shows there was a nearly 2-fold lower total CPK release for tissue treated with ψεRACK peptide.

C. Adminstration of ψεRACK Peptide In Vivo

In another study in support of the invention, the ability of ψεRACK peptide to protect tissue from damage due to an ischemic or hypoxic event was evaluated by administering the peptide in vivo. As detailed in Example 3, ψεRACK peptide (SEQ ID NO:2) or scrambled ψεRACK peptide (SEQ ID NO:4) was administered to adult pigs during the first 10 minutes of a 30 minutes ischemic insult. Five days later, the hearts were analyzed for tissue damage. The results are shown in FIGS. 4A–4C.

Figure 4A:
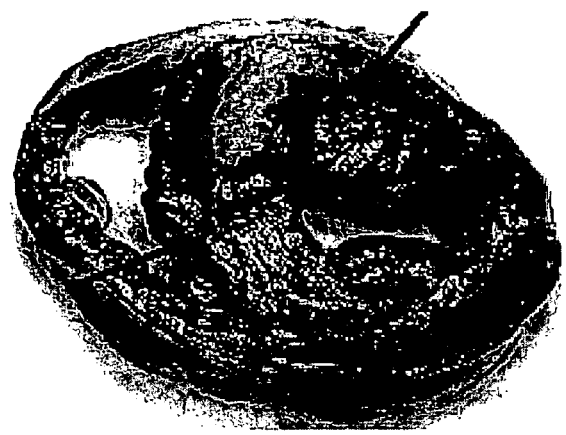
FIGS. 4A–4B are computer generated photos of pig heart slices taken from pigs five days after an in vivo treatment with $\psi$$\epsilon$RACK (FIG. 4A) or with scrambled $\psi$$\epsilon$RACK peptide as a control (FIG. 4B) during the initial 10 minutes of a 30 minute ischemic insult.
Figure 4B:
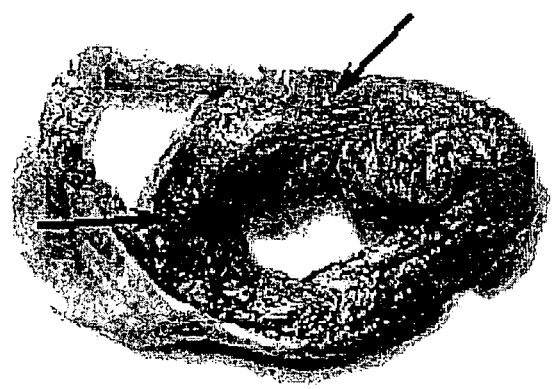

FIGS. 4A–4B are computer-generated photos of pig heart slices taken from the pigs treated in vivo with ψεRACK (FIG. 4A) or with scrambled ψεRACK peptide as a control (FIG. 4B). The hearts were stained with a double-staining technique (Example 3) that allowed determination of the area at risk for ischemic injury (area within the arrows, mainly in the mid wall, in FIG. 4B) and infarcted area (white area in FIG. 4B). As seen in FIG. 4B, control hearts treated with scrambled ψεRACK peptide have a large infarct area within the area at risk (borders shown with arrows). In contrast, pigs that received the ψεRACK peptide (FIG. 4A) have a significantly reduced infarct area. By measuring surface areas and the weights of regions and total tissue weight of areas at risk and infarcted regions, it was determined that the control hearts had an average of 36.5±0.3% infarct of area at risk, whereas hearts treated with ψεRACK peptide had an average of 14.9±0.6% infarct of area at risk (p<0.005).

Figure 4C:
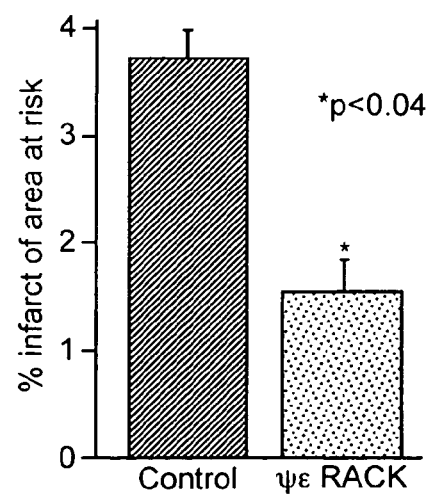
FIG. 4C is a bar graph showing the total infarct area as a percent of area at risk, measured in grams of cardiac tissue, for pigs treated with $\psi$$\epsilon$RACK peptide or with scrambled $\psi$$\epsilon$RACK peptide (control).

FIG. 4C is a bar graph showing the infarct area as a percent of area at risk, measured in grams of cardiac tissue. As seen, the percent infarct was reduced by more than 2-fold for the animals treated with ψRACK peptide. Accordingly, delivery of a ψεRACK peptide in vivo prior to or during an ischemic event is effective to reduce the percentage of infarct by at least 2-fold.

Blood samples and tissue samples of lung, liver, brain, gut, kidney, etc. were collected from the animals and analyzed at a pathology lab. All samples were normal and no inflammation or tissue abnormalities were observed.

Figure 5:
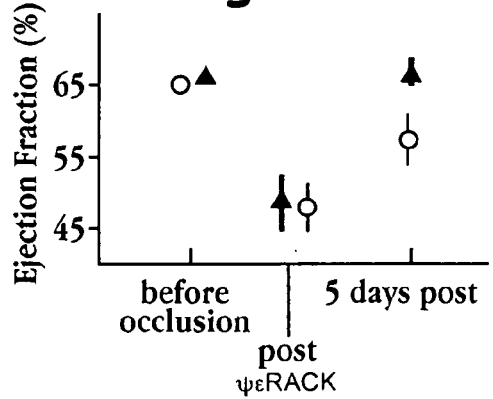
FIG. 5 is a graph showing the ejection fraction, as measured by left ventricurogram in pigs at three time points: (1) before occlusion of left anterior descending artery by balloon catheter (before occlusion); (2) immediately after reperfusion with $\psi$$\epsilon$RACK (post $\psi$$\epsilon$RACK); and (3) before sacrifice five days later (5 days post), for animals treated with ψεRACK (solid triangles) and for control animals treated with a scrambled peptide (open circles).

In another study, left ventricurogram (LVG) was performed in pigs (n=5) at three time points: (1) before occlusion of left anterior descending artery by balloon catheter (before occlusion); (2) immediately after reperfusion with 5 μM/10 mL of ψεRACK (post ψεRACK); and (3) before sacrifice five days later (5 days post), using 6 Fr. of pig-tail catheter. LVG was recorded by two views, right anterior oblique and left anterior oblique. Ejection fraction (EF), the percent of blood ejected in a beat, during maximum contraction, of the total maximum present in the left ventricle, was analyzed by the software, Plus Plus (Sanders Data Systems), and the averages of two views were evaluated. Ejection fractions were calculated based on left ventricle dimensions and the results are shown in FIG. 5. Ejection fraction is a measure of how well the heart is functioning, with a higher ejection fraction indicative of a better functioning heart. An ejection fraction of less than 50% in a short period of time can suggest progression into a state of heart failure. As seen in FIG. 5, animals treated with ψεRACK (closed triangles) had a higher ejection fraction after occlusion compared to the control animals treated with a scrambled peptide (open circles), suggesting the peptide reduces or prevents damage to the cells and tissue due to ischemia. This is also evident from the data point at 5 days post ischemia and treatment, where animals treated with ψεRACK had an ejection fraction on par with that measured prior to ischemia and about 10% higher than the untreated animals. Accordingly, delivery of a ψεRACK peptide in vivo after ischemia is effective to reduce cell and tissue damage, as evidenced by an ejection fraction at least 10% greater than that of untreated cells or tissues.

III. ψεRACK Peptide

As used herein, a "ψεRACK peptide" refers to the peptide represented by SEQ ID NO:2 and to derivatives and fragments of this peptide. Exemplary derivatives are given in SEQ ID NOS:6–18, and include the following sequences: HEADIGYD (SEQ ID NO:6); HDAPIGYE (SEQ ID NO:7); HDAPVGYE (SEQ ID NO:8); HDAPLGYE (SEQ ID NO:9); HDAPIGDY (SEQ ID NO:10); HDAPIGEY (SEQ ID NO:11); ADAPIGYD (SEQ ID NO:12); HDGPIGYD (SEQ ID NO:13); HDAAIGYD (SEQ ID NO:14), and combinations of these modifications.

In one preferred embodiment, the sequence "DAPIG" (SEQ ID NO: 18) in SEQ ID NO:2 is has no more than two modifications at any residue. One, two, or all three of the residues outside the sequence "DAPIG" can be modified. For example, AEAPVGEY (SEQ ID NO:15) is a derivative of SEQ ID NO:2 where all three residues outside the "DAPIG" (SEQ ID NO:18) sequence and two residues within the "DAPIG" sequence are modified. Other examples include HEAPIGDN (SEQ ID NO:16) and HDGDIGYD (SEQ ID NO:17).

It will also be appreciated that fragments of SEQ ID NO:2 and of the modifications described above may be suitable. An exemplary fragment of SEQ ID NO:2 is DAPIG, (SEQ ID NO:18).

All of these exemplary peptides may be (i) chemically synthesized or (ii) recombinantly produced in a host cell using, e.g., an expression vector containing a polynucleotide fragment encoding said peptide, where the polynucleotide fragment is operably linked to a promoter capable of expressing mRNA from the fragment in the host cell.

The dose of peptide administered will vary depending on the tissue to be treated and the condition of the patient. Dosages are readily determined by those of skill in the art based on animal and human studies. Typically, between 0.05–5 µM, more preferably between 0.1–2 µM, most preferably between about 0.1–1 µM peptide is administered. However, the upper and lower limits of these ranges are merely exemplary.

The peptide can be administered by any route suitable, as determine by the primary care provider. For example, administration by intraveneous, parenteral, subcutaneous, inhalation, intranasal, sublingual, mucosal, and transdermal, and the like, is contemplated. Naturally, the route of administration will influence the dose and timing of administration, as appreciated by those of skill.

The peptide can be administered in the form of a fusion protein or a transport protein conjugate. Typically, to form a fusion protein, the peptide is bound to another peptide by a bond other than a Cys-Cys bond. An amide bond from the C-terminal of one peptide to the N-terminal of the other is exemplary of a bond in a fusion protein. The second peptide to which the δPKC agonist/antagonist peptide is bound can be virtually any peptide selected for therapeutic purposes or for transport purposes. For example, it maybe desirable to link the ψεRACK peptide to a cytokine or other peptide that elicites a biological response.

Where the peptide is part of a conjugate, the peptide is typically conjugated to a carrier peptide, such as Tat-derived transport polypeptide (Vives et al., 1997), polyarginine (Mitchell et al., 2000; Rolhbard et al, 2000) or Antennapedia peptide by a Cys-Cys bond. See U.S. Pat. No. 5,804,604. In another general embodiment, the peptide can be introduced to a cell, tissue or whole organ using a carrier or encapsulant, such as a liposome in liposome-mediated delivery.

It will also be appreciated that ψεRACK as well as any compound having similar activity can be used in the methods of treatment described herein. Other compounds, such as peptide mimetics, chemical compounds, or other peptides, can be identified by, for example, a screening method set forth in U.S. Pat. No. 6,165,977, and this portion on Col. 14, line 45–Col 15, line 54 is incorporated by reference herein. In brief, and by way of example for identifying a compound effective to protect a cell or tissue from ischemia, δPKC is immobilized inside the wells of a multiwell plate by introducing a solution containing δPKC into the plate and allowing the δPKC to bind to the plastic. The wells may be precoated with substances that enhance attachment of δPKC and/or that decrease the level of non-specific binding.

The plate is then incubated with a blocking solution (containing, for example bovine serum albumin) and then washed several times. A solution containing reporter-labelled (e.g., radiolabelled of fluorescently-tagged) peptide ψεRACK (SEQ ID NO:2) and, in the test wells, as opposed to the control wells, a test compound is added. Different wells may contain different test compounds or different concentrations of the same test compound. Each test compound at each concentration is typically run in duplicate and each assay is typically run with negative (wells with no test compound) as well as positive (wells where the "test compound" is unlabeled peptide) controls. The free peptide is then washed out, and the degree of binding in the wells is assessed.

A test compound is identified as active it if decreases the binding of the peptide, i.e., if its effect on the extend of binding is above a threshold level. More specifically, if the decrease in binding is a several-fold different between the control and experimental samples, the compound would be considered as having binding activity. Typically, a 2-fold or 4-fold threshold difference in binding between the test and control samples is sought.

Detection methods useful in such assays include antibody-based methods, direct detection of a reporter moiety incorporated into the peptide, such as a fluorescent label, and the like.

A variety of test compounds may be screened, including other peptides, macromolecules, small molecules, chemical and/or biological mixtures, fungal extracts, bacterial extracts or algal extracts. The compounds can be biological or synthetic in origin.

IV. Utility and Routes of Administration

The present invention has application, for example, in treatment of surviving heart attack victims, as well in treatment of persons who presently die from heart disease after admission to the hospital. Delivery of the εPKC selective peptide agonist, ψεRACK, is valuable in the management of these patients, both acutely and chronically.

Acutely, in patients brought to hospital with impending infarction, medical care has traditionally been directed towards removing the cause of coronary occlusion either by thrombolytics or by catheter angioplasty. However, reperfusion of the damaged areas can be one of the major mechanisms of myocardial cellular injury. Administration of a ψεRACK peptide PKC agonist delivered to the site of occlusion by catheter or injected intravenously to induce cardioprotection immediately before or concurrently with thrombolysis or angioplasty is contemplated by the invention.

Chronically, in patients with angina, the current medical approach is to stop the symptoms of angina without replacement of angina's preconditioning protective effect. AεPKC selective agonist, such as ψεRACK, can replace the preconditioning effect induced by angina in these patients and offer a higher rate of myocardial salvage during future episodes of more severe ischemia.

Additional uses of the invention include clinical situations in which the timing of ischemia is physician-controlled. In such instances, pharmacologic enhancement of the preconditioning response would provide a significant advantage to the patients undergoing treatment. Specifically, each year, in the United States alone, 600,000 adults and 12,000 children undergo open heart operations utilizing cardiopulmonary bypass, during which the heart is subjected to periods of controlled ischemia ranging from several minutes to well over one hour. Despite advances in cardiac protection, myocardial dysfunction during the immediate post-operative period remains a leading cause of morbidity and mortality in these patients. The exact timing of the ischemic insult is known ahead of time in these patients, allowing for administration of a ψεRACK peptide prior to ischemia. Administration of ψεRACK will reduce myocardial damage by inducing a preconditioning response in the hours, or days, prior to surgery.

Similar benefits could be realized in the area of cardiac transplantation, of which there are approximately 2500 cases annually in the U.S. Prolonged graft ischemia is one of the factors limiting long-distance donor organ acquisition for such cardiac transplantation. Administration of ψεRACK peptide at the time of organ procurement could extend the time between organ harvest and implantation and reduce the risk of post-operative myocardial dysfunction.

It will, of course, be understood that a ψεRACK peptide may employed in the treatment of a variety of ischemic and hypoxic conditions, in addition to cardiac ischemia. For example, ψεRACK may be administered prior to, during or after an ischemic or hypoxic event to a wide variety of cells and tissues. Without intending to be limiting, examples include the kidney, the vascular endothelium, the liver, the eye, and in the central nervous system, where tissue damage to the brain and other tissues of the central nervous system may result due to stroke.

As demonstrated by the studies described herein, the peptide can be administered before, during or after an ischemic or hypoxic event. When delivered before an ischemic insult, the peptide effectively reduces the extent of cellular damage. Preferably, the peptide is perfused over or through the tissue for about 1–180 minutes, more preferably for about 1–120 minutes, most preferably for about 1–60 minutes, prior to the ischemic insult. In one embodiment, a period of time not greater than about three hours, more preferably not greater than about 120 minutes, and most preferably not greater than about 60 minutes, lapses between cessation of peptide perfusion and the ischemic or hypoxic event. The peptide can be delivered for a 1 minute, 2 minute, 5 minute, 10 minute, 20 minute, 30 minute, or longer, period of time prior to the ischemic insult.

When the peptide is delivered subsequent to an ischemic event, in a preferred embodiment a period of time not greater than about two hours, more preferably not greater than one hour, and even more preferably not greater than 30 minutes lapses between the ischemic event and initiation of administration of the peptide. The peptide can be delivered for a 1 minute, 2 minute, 5 minute, 10 minute, 20 minute, 30 minute, or longer, period of time following the ischemic insult.

The peptide can also be administered during an ischemic event. Particularly, during time of controlled ischemia, such as during surgery, the care provider can initiate administration of the ψεRACK peptide just prior to or concurrent with initiation of the ischemic event.

V. EXAMPLES

The following examples further illustrate the invention described herein and are in no way intended to limit the scope of the invention.

Methods

1. Peptide Preparation

ψεRACK (HDAPIGYD, SEQ ID NO:2) was synthesized and purified (>95%) at the Stanford Protein and Nucleic Acid Facility. Scrambled ψεRACK peptide (PDYHDAGI, SEQ ID NO:4) was prepared similarly. In some studies, the peptides were modified with a carrier peptide by cross-linking via an N-terminal Cys-Cys bond to the *Drosophila* Antennapedia homeodomain-derived peptide (C-RQIKIWFQNRRMKWKK, SEQ ID NO:3; Théodore, L. et al., 1995; Johnson, J. A. et al., 1996a) or via an N-terminal Cys-Cys bond to Tat protein-derived peptide (C-YGRKKRRQRRR, SEQ ID NO:6).

Example 1

Ex Vivo Administration of ψεRACK Prior to Ischemia

Mice or rats were anesthetized with i.p. avertin, and their hearts were rapidly removed and cannulated via the aorta for reperfusion as described in the art (Colbert et al, 1997). Care was taken to have the hearts perfused within 90 seconds of removal. The left ventricular pressure and real-time derivative (dP/dt) were monitored via a catheter placed in the ventricular apex. Hemodynamic parameters were archived every 20 seconds throughout the procedure. The hearts were perfused with oxygenated Krebs-Henseleit solution comprised of, in nmol/L, NaCl 120; KCl 5.8; NaHCO$_3$ 25; NaH$_2$O$_4$ 1.2; MgSO$_4$ 1.2; CaCl$_2$ 1.0; and dextrose 10, pH 7.4 at 37 C.

After a 10–20 minute equilibration period, the hearts were treated with ψεRACK peptide (SEQ ID NO:2) or with scrambled ψεRACK peptide (SEQ ID NO:4) for 20 minutes. Perfusion was maintained at a constant flow of 10 mL/min with Krebs-Henseleit solution containing 0.5 εM of the appropriate peptide. The Langendorff method employed used retrograde flow from the ventricle to the aorta and into the coronary arteries, bypassing the pulmonary arteries.

To induce global ischemia, flow was interrupted for 45 minutes. After the ischemic event, the hearts were reperfused with Krebs-Henseleit solution for 30–160 minutes. During reperfusion, ischemia-induced cell damage was determined by measuring the activity of creatine phosphokinase (CPK) (absorbance at 520 nm) in the perfusate using a Sigma kit. The results are shown in FIGS. 1A–1B.

Example 2

Ex Vivo Administration of ψεPKC After to Ischemia

Rat hearts were prepared as described in Example 1. After a 30 minute equilibration period, global ischemia was induced by interrupting fluid flow for 45 minutes. The hearts were then reperfused with 0.5 μM of ψεRACK peptide for 20 minutes, followed by 40 minutes of reperfusion without the peptide. As a control, some hearts were left untreated after ischemia. During the 60 minute period following ischemia, ischemia-induced cell damage was determined by monitoring the creatine phosphokinase (CPK) activity (absorbance at 520 nm) in the perfusate collected during reperfusion. The results are shown in FIGS. 3A–3B.

Example 3

In Vivo Administration of ψεPKC Prior to Ischemia

Young adult female pigs, 35–40 kg in weight, were anesthetized and a catheter was introduced through the carotid artery into the heart. Using conventional intervention cardiology techniques, a wire was placed through a catheter and into the left anterior descending artery (LAD). A balloon was run over this wire to a site of occlusion where it was then inflated to block blood flow for 30 minutes. During the first 10 minutes of the ischemic insult, either the control scrambled ψεRACK peptide (SEQ ID NO:4, n=5) or the biologically active ψεRACK peptide (SEQ ID NO:2, n=5) was delivered by diffusion through the balloon directly downstream of the occlusion. Approximately 20 μg peptide (~400 ng per kg body weight) was administered.

After 30 minutes of occlusion, the balloon was removed and pigs were left to recover from surgery. Five days later, the pigs were euthanized and hearts were harvested. After heart removal, the LAD was occluded. With the occlusion in place, Evans Blue dye, which stains all areas not at risk of infarct in blue while leaving all areas with no access to blood flow red, was infused. Hearts were then cut into slices and stained with a tetrazolium red dye which stains all live areas red and infarcted dead tissue in white. Each heart had multiple tissue slices with distinctive areas marking the area at risk for ischemia and the infarcted area. From this the percent infarct per area at risk for each slice and for the entire heart was determined. The results are shown in FIGS. 4A–4C.

Although the invention has been described with respect to particular embodiments, it will be apparent to those skilled in the art that various changes and modifications can be made without departing from the invention.

It is claimed:

1. A composition comprising a peptide having a sequence that shares at least 50% identity with SEQ ID NO: 2, said peptide having the ability to selectively activate epsilon protein kinase C (εPKC) function in cardiac myocytes, said peptide attached by an N-terminal cysteine residue to a Tat-derived peptide or to a polyarginine peptide.

2. The composition of claim 1, wherein said peptide shares a sequence that is at least 70% identity with SEQ ID NO: 2.

3. The composition of claim 1, wherein said peptide shares a sequence that is at least 80% identity with SEQ ID NO: 2.

4. The composition of claim 1, wherein said Tat-derived peptide has a sequence identified as SEQ ID NO:5.

5. A method for reducing in vivo damage due to ischemia, hypoxia, or reperfusion injury in a subject, comprising administering to said subject the peptide according to claim 1.

6. The method of claim 5, wherein said administering is by a route selected from the group consisting of intravenous, parenteral, subcutaneous, inhalation, intranasal, sublingual, mucosal, and transdermal.

7. The method of claim 5, wherein said administering is by infusion through coronary arteries to the heart.

8. The method of claim 5, wherein said administering comprises administering the peptide prior to ischemia, hypoxia, or reperfusion.

9. The method of claim 5, wherein said administering comprises administering the peptide after ischemia, hypoxia, or reperfusion.

10. The method of claim 5, wherein said administering comprises administering the peptide during ischemia, hypoxia, or reperfusion.

11. A method for reducing in vivo damage to an organ due to ischemia, hypoxia, or reperfusion injury in a subject, comprising administering to said subject the peptide according to claim 1.

12. The method of claim 11, wherein the method is for reducing damage to an organ selected from the group consisting of heart, lung, liver, brain, and kidney.

13. The method of claim 11, wherein said administering is by a route selected from the group consisting of intravenous, parenteral, subcutaneous, inhalation, intranasal, sublingual, mucosal, and transdermal.

14. The method of claim 11, wherein said administering is by infusion through coronary arteries to the heart.

15. The method of claim 11, wherein said administering comprises administering the peptide prior to ischemia, hypoxia, or reperfusion.

16. The method of claim 10, wherein said administering comprises administering the peptide after ischemia, hypoxia, or reperfusion.

17. The method of claim 10, wherein said administering comprises administering the peptide during ischemia, hypoxia, or reperfusion.

18. A method for reducing in vivo cellular damage due to ischemia, hypoxia, or reperfusion injury in a subject, comprising administering to said subject the peptide according to claim 1.

19. The method of claim 18, wherein the method is for reducing damage to cells selected from the group consisting of heart, lung, liver, brain, and kidney.

20. The method of claim 18, wherein said administering is by a route selected from the group consisting of intravenous, parenteral, subcutaneous, inhalation, intranasal, sublingual, mucosal, and transdermal.

21. The method of claim 18, wherein said administering is by infusion through coronary arteries to the heart.

22. The method of claim 18, wherein said reducing is reducing cellular damage to cardiomyocytes.

23. The method of claim 18, wherein said administering comprises administering the peptide prior to ischemia, hypoxia, or reperfusion.

24. The method of claim 18, wherein said administering comprises administering the peptide after ischemia, hypoxia, or reperfusion.

25. The method of claim 18, wherein said administering comprises administering the peptide during ischemia, hypoxia, or reperfusion.

26. A method for reducing damage to an ex vivo organ due to ischemia, hypoxia, or reperfusion injury, comprising administering to said organ the peptide according to claim 1.

27. The method of claim 26, wherein the method is for reducing damage to an organ selected from the group consisting of heart, lung, liver, brain, and kidney.

28. The method of claim 26, wherein said administering comprises administering the peptide prior to ischemia, hypoxia, or reperfusion.

29. The method of claim 26, wherein said administering comprises administering the peptide after ischemia, hypoxia, or reperfusion.

30. The method of claim 26, wherein said administering comprises administering the peptide during ischemia, hypoxia, or reperfusion.

31. A method for reducing damage to a cell due to ischemia, hypoxia, or reperfusion injury, comprising administering to said cell the peptide according to claim 1.

32. The method of claim 31, wherein the method is for reducing damage to a cell selected from the group consisting of heart cells, lung cells, liver cells, brain cells, and kidney cells.

33. The method of claim 31, wherein said administering comprises administering the peptide prior to ischemia, hypoxia, or reperfusion.

34. The method of claim 31, wherein said administering comprises administering the peptide after ischemia, hypoxia, or reperfusion.

35. The method of claim 31, wherein said administering comprises administering the peptide during ischemia, hypoxia, or reperfusion.

* * * * *

SEQUENCE LISTING

<160> NUMBER OF SEQ ID NOS: 18

<210> SEQ ID NO 1
<211> LENGTH: 8
<212> TYPE: PRT
<213> ORGANISM: Artificial Sequence
<220> FEATURE:
<223> OTHER INFORMATION: epsilon V1-2, residues 14-21 of epsilon-PKC

<400> SEQUENCE: 1

Glu Ala Val Ser Leu Lys Pro Thr
1               5

<210> SEQ ID NO 2
<211> LENGTH: 8
<212> TYPE: PRT
<213> ORGANISM: Artificial Sequence
<220> FEATURE:
<223> OTHER INFORMATION: pseudo-epsilon RACK octapeptide

<400> SEQUENCE: 2

His Asp Ala Pro Ile Gly Tyr Asp
1               5

<210> SEQ ID NO 3
<211> LENGTH: 16
<212> TYPE: PRT
<213> ORGANISM: Artificial Sequence
<220> FEATURE:
<223> OTHER INFORMATION: Drosophila antennapedia homeodomain-derived
      carrier peptide

<400> SEQUENCE: 3

Arg Gln Ile Lys Ile Trp Phe Gln Asn Arg Arg Met Lys Trp Lys Lys
1               5                   10                  15

<210> SEQ ID NO 4
<211> LENGTH: 8
<212> TYPE: PRT
<213> ORGANISM: Artificial Sequence
<220> FEATURE:
<223> OTHER INFORMATION: scrambled pseudo-epsilon RACK octapeptide

<400> SEQUENCE: 4

Pro Asp Tyr His Asp Ala Gly Ile
1               5

<210> SEQ ID NO 5
<211> LENGTH: 11
<212> TYPE: PRT
<213> ORGANISM: Artificial Sequence
<220> FEATURE:
<223> OTHER INFORMATION: Tat-derived carrier peptide

<400> SEQUENCE: 5

Tyr Gly Arg Lys Lys Arg Arg Gln Arg Arg Arg
1               5                   10

<210> SEQ ID NO 6
<211> LENGTH: 8
<212> TYPE: PRT
<213> ORGANISM: Artificial Sequence
<220> FEATURE:
<223> OTHER INFORMATION: modified pseudo-epsilon RACK peptide

<400> SEQUENCE: 6

His Glu Ala Asp Ile Gly Tyr Asp
1               5

<210> SEQ ID NO 7
<211> LENGTH: 8
<212> TYPE: PRT
<213> ORGANISM: Artificial Sequence
<220> FEATURE:
<223> OTHER INFORMATION: modified pseudo-epsilon RACK peptide

<400> SEQUENCE: 7

His Asp Ala Pro Ile Gly Tyr Glu
1               5

<210> SEQ ID NO 8
<211> LENGTH: 8
<212> TYPE: PRT
<213> ORGANISM: Artificial Sequence
<220> FEATURE:
<223> OTHER INFORMATION: modified pseudo-epsilon RACK peptide

<400> SEQUENCE: 8

His Asp Ala Pro Val Gly Tyr Glu
1               5

<210> SEQ ID NO 9
<211> LENGTH: 8
<212> TYPE: PRT
<213> ORGANISM: Artificial Sequence
<220> FEATURE:
<223> OTHER INFORMATION: modified pseudo-epsilon RACK peptide

<400> SEQUENCE: 9

His Asp Ala Pro Leu Gly Tyr Glu
1               5

<210> SEQ ID NO 10
<211> LENGTH: 8
<212> TYPE: PRT
<213> ORGANISM: Artificial Sequence
<220> FEATURE:
<223> OTHER INFORMATION: modified pseudo-epsilon RACK peptide

<400> SEQUENCE: 10

His Asp Ala Pro Ile Gly Asp Tyr
1               5

<210> SEQ ID NO 11
<211> LENGTH: 8
<212> TYPE: PRT
<213> ORGANISM: Artificial Sequence
<220> FEATURE:
<223> OTHER INFORMATION: modified pseudo-epsilon RACK peptide

<400> SEQUENCE: 11

His Asp Ala Pro Ile Gly Glu Tyr
1               5

<210> SEQ ID NO 12
<211> LENGTH: 8
<212> TYPE: PRT
<213> ORGANISM: Artificial Sequence
<220> FEATURE:
<223> OTHER INFORMATION: modified pseudo-epsilon RACK peptide

<400> SEQUENCE: 12

```
Ala Asp Ala Pro Ile Gly Tyr Asp
 1               5
```

<210> SEQ ID NO 13
<211> LENGTH: 8
<212> TYPE: PRT
<213> ORGANISM: Artificial Sequence
<220> FEATURE:
<223> OTHER INFORMATION: modified pseudo-epsilon RACK peptide

<400> SEQUENCE: 13

```
His Asp Gly Pro Ile Gly Tyr Asp
 1               5
```

<210> SEQ ID NO 14
<211> LENGTH: 8
<212> TYPE: PRT
<213> ORGANISM: Artificial Sequence
<220> FEATURE:
<223> OTHER INFORMATION: modified pseudo-epsilon RACK peptide

<400> SEQUENCE: 14

```
His Asp Ala Ala Ile Gly Tyr Asp
 1               5
```

<210> SEQ ID NO 15
<211> LENGTH: 8
<212> TYPE: PRT
<213> ORGANISM: Artificial Sequence
<220> FEATURE:
<223> OTHER INFORMATION: modified pseudo-epsilon RACK peptide

<400> SEQUENCE: 15

```
Ala Glu Ala Pro Val Gly Glu Tyr
 1               5
```

<210> SEQ ID NO 16
<211> LENGTH: 8
<212> TYPE: PRT
<213> ORGANISM: Artificial Sequence
<220> FEATURE:
<223> OTHER INFORMATION: modified pseudo-epsilon RACK peptide

<400> SEQUENCE: 16

```
His Glu Ala Pro Ile Gly Asp Asn
 1               5
```

<210> SEQ ID NO 17
<211> LENGTH: 8
<212> TYPE: PRT
<213> ORGANISM: Artificial Sequence
<220> FEATURE:
<223> OTHER INFORMATION: modified pseudo-epsilon RACK peptide

<400> SEQUENCE: 17

```
His Asp Gly Asp Ile Gly Tyr Asp
 1               5
```

<210> SEQ ID NO 18
<211> LENGTH: 5
<212> TYPE: PRT
<213> ORGANISM: Artificial Sequence

```
-continued

<220> FEATURE:
<223> OTHER INFORMATION: pseudo-epsilon RACK peptide fragment

<400> SEQUENCE: 18

Asp Ala Pro Ile Gly
 1               5
```